United States Patent [19]
Hopewell

[11] Patent Number: 5,345,772
[45] Date of Patent: Sep. 13, 1994

[54] SINGLE COLUMN DISTILLATIVE SEPARATION EMPLOYING BOTTOM ADDITIVES

[75] Inventor: Richard B. Hopewell, Medfield, Mass.

[73] Assignee: Process Systems International, Inc., Westborough, Mass.

[21] Appl. No.: 62,959

[22] Filed: May 14, 1993

[51] Int. Cl.$^5$ .............................................. F25J 3/00
[52] U.S. Cl. .................................. 62/20; 62/29
[58] Field of Search ........................... 62/17, 20, 29

[56] References Cited

U.S. PATENT DOCUMENTS

| | | | |
|---|---|---|---|
| Re. 32,600 | 2/1988 | Ryan et al. | 62/17 |
| 4,383,841 | 5/1983 | Ryan et al. | 62/20 |
| 4,383,842 | 5/1983 | O'Brien | 62/20 |
| 4,881,960 | 11/1989 | Ranke | 62/20 |

*Primary Examiner*—Ronald C. Capossela
*Attorney, Agent, or Firm*—Richard P. Crowley

[57] ABSTRACT

A method for the distillative separation of hydrocarbon feed stream such as a carbon dioxide-containing feed stream in a single distillation column into a vapor carbon dioxide product stream and a side column product stream such as a liquid propane stream employing a recycled C4+ bottom additive stream. The method comprises: Introducing a feed stream into a single cryogenic distillation column; withdrawing a C4+ bottom additive stream from the bottom of the column; recycling the C4+ stream into the single column above the feed point of the feed stream, and withdrawing from a side point in the column above the introduction of the feed stream a vapor product stream enriched in C3+, and cooling the vapor stream to produce a C3 liquid product stream.

17 Claims, 1 Drawing Sheet

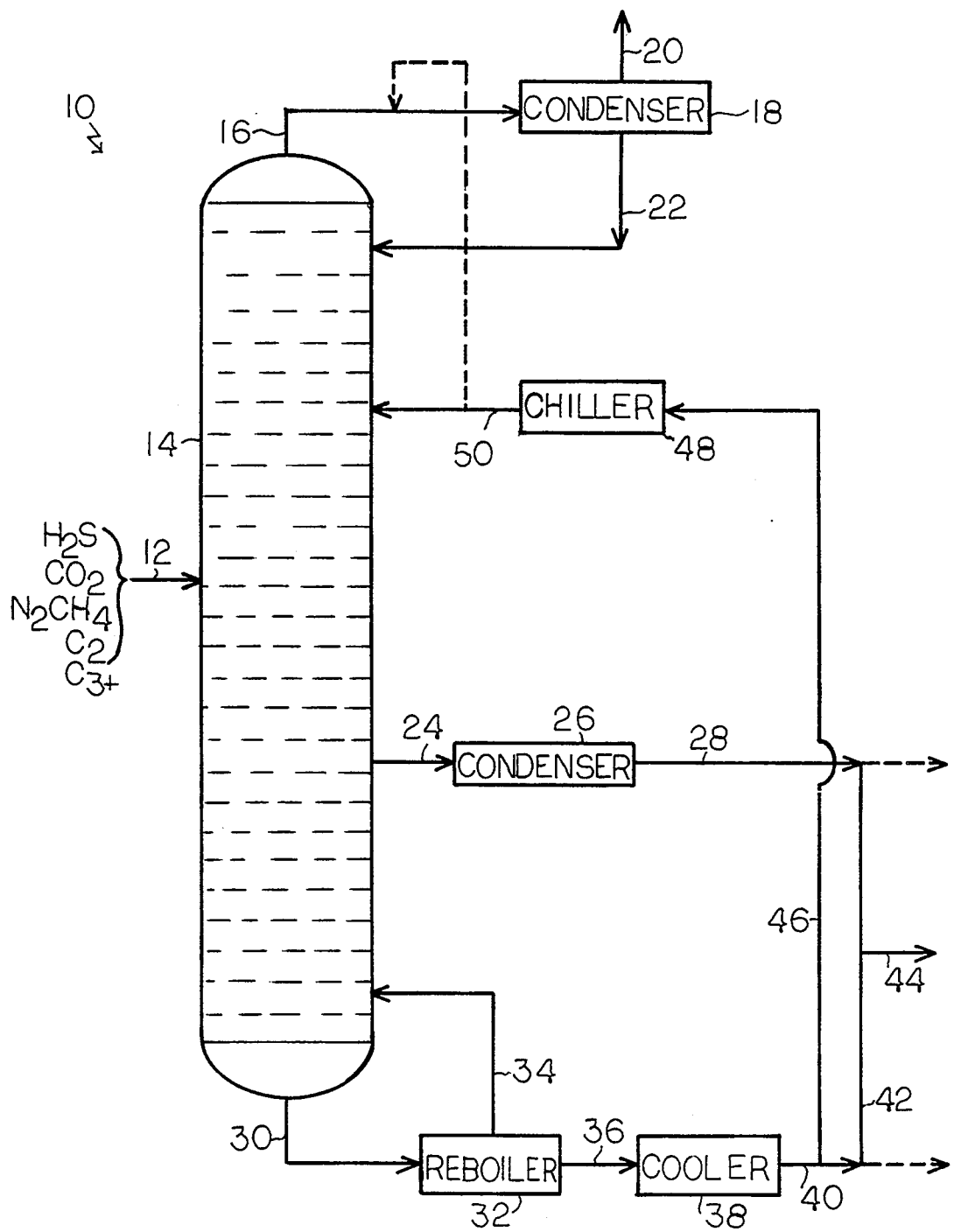

SINGLE COLUMN DISTILLATIVE SEPARATION EMPLOYING BOTTOM ADDITIVES

BACKGROUND OF THE INVENTION

U.S. Patent RE32,600, issued Feb. 16, 1988, hereby incorporated by reference in its entirety, discloses a distillative cryogenic separation method employing a bottom additive stream. The method is directed to a hydrocarbon-containing feed stream, and is directed toward the production of overhead and bottom product streams, both to desired specifications. The method comprises recycling a portion of a bottom product stream, typically but not necessarily derived from the separation process, back into the upper portion of the column or into the reflux condenser. The distillative separation method described provides for a savings of energy and provides for the adjustment in the column operating conditions, such as the column operating pressure or temperatures. The distillation separation method employs a nonpolar liquid additive agent, typically a C4+ stream, that is, a stream composed of C4 or higher alkanes. This distillative separation method is particularly directed to the separation of methane and nitrogen from a natural gas hydrocarbon stream, and, in another embodiment, the separation of a carbon dioxide-containing feed stream to recover a C3+ stream, and is also directed to recovering a C4+ stream having lower amounts of recovered components, such as lower amounts of hydrogen sulfide, ethane, or propane therein.

The distillative separation method, employing the bottom additive as described, comprises a two-column system; the first column representing a high pressure recovery column, typically operated for propane plus (C3+) recovery, hydrogen sulfide removal, or ethane (C2+) recovery, and a lower pressure additive recovery column, operated to recover a C4+ stream and to permit recycling of a portion of the C4+ stream as a bottom additive to the high pressure recovery column. This two-column system, by its nature, requires a multitude of processing equipment, including, as a minimum, two distillation columns, two overhead condensing systems (condensers, reflux accumulator drums and reflux pumps) and two bottom reboilers. In addition, the two-column system requires a multitude of instrumentation for control and system monitoring.

It is therefore desirable to provide for a new and improved distillation separation method employing a bottom additives stream. The method, as described, is particularly directed to, but not limited to, the propane recovery separation.

SUMMARY OF THE INVENTION

The present invention is directed to a single column distillative separation of a hydrocarbon stream into an overhead stream, a sidedraw-product stream, and a bottom-product stream, which single column separation employs a recycled bottom-additive stream. In particular, the invention concerns a method for the distillative separation of a carbon dioxide-containing hydrocarbon stream, in a single distillation column, into a carbon dioxide product stream, a propane (C3+) side product and a C4+ bottom product; e.g., a C4/C9 alkane stream. A portion of the C4+ bottom product is recycled to the upper portion of the distillation column as a bottom additive; the balance of the C4+ bottom product may be recovered as a separate product or combined with the C3+ side product.

The method of the invention is directed to a method for the distillative separation of a hydrocarbon feed stream, such as a carbon dioxide-containing hydrocarbon feed stream, in a single distillation column, typically containing mass transfer fluid contacting devices such as trays, loose packing, structural packing, or a combination thereof. The separation of said feed produces an overhead product stream, typically a carbon dioxide product overhead stream of defined specifications, a propane-containing product recovery stream, and a bottom product stream deficient in propane. The method comprises introducing the feed stream into a single cryogenic distillation column, removing a C4+ bottoms liquid stream, cooling a portion of the reboiled C4+ bottom stream, and then introducing the cooled C4+ stream, as a liquid additive stream, into the upper portion of the column, at a location above the incoming feed stream, or into the overhead reflux condenser. The C4+ stream is typically composed of component materials recovered from the incoming feed stream, but may comprise outside C4+ materials which are introduced into the system and which may be continuously or intermittently added to offset the material losses which may be removed with the vapor recovery product. To facilitate the enhanced separation operation, the C4+ bottom additive is generally produced deficient in the component material to be recovered: for example, in the propane recovery operation, the C4+ additive should contain, typically, less than one molar percent propane. The relative concentration of the heavier component, for example, the butanes, may be adjusted based upon economic considerations; as such, the C4 content of the C4+ additive may be as high as 12 molar percent of greater, or as low as i molar percent or less.

The method includes removing from the overhead of the single distillation column a vapor stream, such as a carbon dioxide-enriched vapor, and cooling the enriched product stream, such as the carbon dioxide-enriched product stream, to produce a liquid stream, such as a liquid carbon dioxide stream, and a vapor product stream. The method includes recycling the cooled liquid stream, such as the cool liquid carbon dioxide stream, into the upper portion of the distillation column, above the introduction point of the C4+ bottom additive stream, such as into the upper 20% of the column, and then recovering the overhead vapor carbon dioxide product stream. If so desired or if economically justified, the C4+ bottom additive may be injected into the column overhead vapor, prior to cooling; the resulting liquid, which is separated from the overhead vapor product, then contains C4+ additives plus an additional amount of carbon dioxide liquid and is recycled to the top of the distillation column.

The method further includes withdrawing of a vapor stream, such as a vapor C3+ stream of defined specification, at a point below the introduction of the feed stream; for example, where there is little, if any, carbon dioxide and/or hydrogen sulfide. The method comprises cooling the C3+ vapor stream and withdrawing a liquid C3+ recovery product stream of defined specification. In the withdrawal from the column of the vapor recovery product stream, such as the vapor C3+ stream, the amount of contaminants in the vapor stream may vary depending upon the economic specifications of the operation of the column, and, for example, typically in withdrawing a C3+ vapor stream, generally there is little if any carbon dioxide and/or hydrogen sulfide, such as, as low as 50 parts per million, or as much as 2 molar percent or more depending on the economic incentives of operating the column.

Generally, the hydrocarbon-containing carbon dioxide feed stream is derived from a carbon dioxide-enhanced oil recovery flood operation. The traditional method for the distillative separation of carbon dioxide and ethane to recover a propane recovery product stream employing a C4+ bottom additive stream uses a high pressure recovery column, typically operating at 250-350 psig, and a lower pressure additive recovery column, typically operating at 100-200 psig. Generally, the additive recovery column is designed to provide a rather sharp separation between the C4 and C5 fractions of the C4+ bottom additive stream. Typically, the additive column overhead product containing the bulk of the recovered C3 and C4 fractions is then remixed with the net C4+ essence bottom product to produce a single, combined Natural Gas Liquid (NGL) product. The traditional two-column system must contain its own auxiliary equipment items, such as condensers, reflux accumulators, pumps, reboilers, controls, instrumentation and so forth, as well as incur all the additional engineering and design costs to construct or operate the two-column distillation system. The new, single column method allows the recovery and additive separation to occur in a single, distillative fractionation column, and which single column and method provides for new and unexpected savings in material, energy, operating and design specification costs. In the single column distillate method, the bulk of the recovered hydrocarbons, that is the C3+ vapor stream, is withdrawn from the column as the sidedraw vapor product stream. The bottom additive and a heavier purge stream are taken out as a bottom product stream. While the single column itself may be slightly taller to accommodate additional bottom staging, there is an overall reduction in the total column installed equipment cost, a reduction in the system engineering cost due to the fewer components required, an overall net heat savings and a lower power consumption. Further, since there is only a single reboiler, it may be desirable to utilize a direct-fired reboiler an thus eliminate the additional equipment items associated with a separately fired, circulating hot oil or steam-raising system for the reboiler. The significant material, operating, energy and engineering cost reductions provide a new and unique method for the separation of hydrocarbons, particularly for the separation of carbon dioxide and for the recovery of a (C3+ propane recovery) stream employing an additive stream.

The hydrocarbon feed stream useful in the single column method is directed in one embodiment to high content carbon dioxide-containing hydrocarbon feed streams, however the method may also be used for carbon dioxide/ethane, carbon dioxide/hydrogen sulfide and other separations. For such other separations like the carbon dioxide/ethane and carbon dioxide/hydrogen sulfide separations, the vapor sidedraw stream removed from the column comprises a C2/C3 stream or a C2/C3/H2S stream. These lighter components in the sidedraw stream would not be condensed in the side reboiler and the heat recovery would be different than for the carbon dioxide/propane separator method. The feed stream may not contain or be directed to the separation of carbon dioxide, but may, for example, comprise a hydrocarbon hydrogen stream or a hydrocarbon methane stream for the separation of hydrogen or methane as the overhead product.

The bottom additive stream produced may also be used in another separate column or system, for example, for other separations such as, but not limited to, cryogenic methane/carbon dioxide separations.

The invention will be described for the purpose of illustration only in connection with certain illustrated embodiments; however, it is recognized that those persons skilled in the art may make various modifications, changes, additions and improvements without departing from the spirit and scope of the invention.

BRIEF DESCRIPTION OF THE DRAWING

The drawing is a schematic illustration of a single column method for the distillative separation of a carbon dioxide-containing hydrocarbon feed stream to provide a propane recovery stream, employing a recycled bottom additive stream.

DESCRIPTION OF THE EMBODIMENT

With reference to the drawing, there is shown a feed line 12 for the introduction of a carbon dioxide-containing hydrocarbon feed stream, typically operating at a temperature from 50° to 150° F. and 250-350 psig, which is directed into a cryogenic distillation column 14 containing a plurality of distillation vapor-liquid contacting devices therein, such as distillation trays or packing. A vapor overhead stream is removed from the column top through line 16 and is introduced into a reflux condenser 18; a liquid portion of the overhead stream is recycled to the top of the column through line 22, while an enriched carbon dioxide overhead product stream is removed through line 20, with a temperature of −20° to +20° F. and 240 to 340 psig.

A column bottom stream is removed through line 30 and is introduced into a reboiler 32; a portion is recycled through line 34 to the bottom of the column, while a bottom product stream is removed through line 36, with a temperature of 320° to 450° F. and 255 to 355 psig. The bottom product consists of an alkane mixture comprising a C4+ stream, primarily, but not necessarily, a mixture of C5 to C7 alkanes. The C4+ bottoms is taken through cooler 38 via line 40 at a temperature of 90° to 150° F. and is split into recycle C4+ additive line 46 and a net C4+ bottoms product stream line 42. The recycle additive is further cooled in chiller 48 and introduced in the upper portion of the column 14, above the introduction of the feed line 12, or it may be introduced into the reflux condenser 18, or into both the upper portion of the column and the reflux condenser, to provide for the recycling of the C4+ bottom additive and to provide for the enhanced distillative separation.

A side vapor stream is removed through line 24, at a temperature of 150° to 250° F. In the operation of the column for propane recovery, the side stream consists of a mixture of C3+, predominantly a mixture of propane and butanes with additional other heavier hydrocarbons. Typically, the withdrawal of the C3+ vapor stream from the column 14 is from a point below the introduction of the feed line 12, and at a location suitable for the economic separation of the recovered hydrocarbons from the undesirable lighter constituents, typically, carbon dioxide and/or hydrogen sulfide. The C3+ is cooled and partially or totally condensed in condenser 26; the C3+ product stream is taken through line 28 at a temperature of 90° to 150° F., either as a separate product stream, or combined with the net C4+ bottoms stream as a single recovered product stream through line 44, at a temperature of 90° to 150° F. and 220 to 320 psig.

As described and illustrated, the process 10 provides for a single, cryogenic, distillative column separation system, which provides for the enhanced separation of a carbon dioxide-containing hydrocarbon feed into a carbon dioxide overhead product stream and a propane recovery product stream. The process 10 provides for the separation and recycling of the bottom additive C4+ stream to occur in a single, cryogenic column. The majority of the recovered hydrocarbons are removed from the column 14 as a sidedraw product stream 28, with a lower flow rate, heavier purge stream 42 taken from the column bottoms. The single column system, as illustrated, thus provides for significant savings in installed equipment costs, instrumentation and controls costs, engineering, construction and maintenance costs, provides for a net heat savings and lower power consumption, and yet provides efficient and effective separation of the desired components from the hydrocarbon feed stream.

Results of computer simulation of the process as illustrated are shown in Table I. The simulation shows the propane recovery mode of operation producing a combined NGL recovery product with low total acid gas (carbon dioxide and hydrogen sulfide) content. The software simulation computer program employed was Process SM, Version 4.01, simulation program from Simulation Sciences, Inc., of Fullerton, Calif.

f) withdrawing from the column bottom a bottom product stream comprising primarily C4+ alkanes;

g) reboiling at least a portion of the withdrawn bottom product stream and recycling at least a portion of the bottom product stream to the bottom portion of the distillative column; and h) splitting the column bottom product stream into a majority, recycled bottom additive stream as in 1(b) and a minor, net heavy component recovery product stream.

2. The method of claim 1 wherein the amount of recycled liquid bottom product stream ranges from about 1 to 30 mols per 100 mols of feed stream.

3. The method of claim 1 wherein the recycled liquid bottom product stream comprises a majority of C4–C9 alkanes.

4. The method of claim 1 wherein the recycled liquid bottom product stream comprises, at least in part, C4+ materials recovered from the feed stream.

5. The method of claim 1 wherein the recycled liquid bottom product stream comprises C4+ component materials continuously or intermittently introduced into the column to account for material losses.

6. The method of claim 1 wherein the recycled liquid bottom product stream is introduced into the overhead condenser.

7. The method of claim 1 wherein the withdrawn side vapor recovery product stream is cooled and partially or totally condensed.

8. The method of claim 7 wherein at least a portion of

TABLE I

| | FLOW RATES - LB MOLES/HR | | | | | |
|---|---|---|---|---|---|---|
| | <12> | <20> | <28> | <42> | <44> COMBINED | <46> |
| | FEED | OVERHEAD PRODUCT | SIDE RECOVERY PRODUCT | NET BOTTOMS PRODUCT | NGL PRODUCT | RECYCLE ADDITIVE |
| H2S | 32.06 | 31.90 | 0.16 | — | 0.16 | — |
| CO2 | 1825.70 | 1825.70 | — | — | — | — |
| N2 + C1 | 72.46 | 72.46 | — | — | — | — |
| C2 | 70.27 | 70.01 | 0.26 | — | 0.26 | — |
| C3 | 85.64 | 8.56 | 77.02 | 0.06 | 77.08 | 0.17 |
| C4'S | 50.51 | 0.22 | 47.33 | 2.96 | 50.29 | 8.69 |
| C5'S | 26.35 | — | 12.88 | 13.47 | 26.35 | 39.58 |
| C6'S | 19.76 | — | 4.35 | 15.41 | 19.76 | 45.29 |
| C7+ | 13.18 | — | 1.62 | 11.56 | 13.18 | 33.94 |
| TOTAL | 2195.93 | 2008.85 | 143.62 | 43.46 | 187.08 | 127.67 |

What is claimed is:

1. A method for the distillative cryogenic separation of a hydrocarbon feed stream comprising CO2, C2, C3 and C4+ and employing a recycled bottom additive in a single distillative column containing vapor-liquid contacting devices, which method comprises:
    a) introducing the feed stream into a single distillative column;
    b) introducing a nonpolar liquid C4+ alkane additive agent into the upper portion of the column above the point of introduction of the feed stream;
    c) withdrawing an overhead product stream enriched in CO2 from the feed stream;
    d) condensing at least a portion of the condensed overhead product stream in a condenser and recycling a portion of the condensed overhead stream to the top portion of the distillative column;
    e) withdrawing a vapor side product stream, enriched in C2 or C3, and deficient in CO2 from the feed stream, at a point below the point of introduction of the feed stream, and substantially above the bottom of the column;

the side product cooling duty is used to provide heat input to the distillative column.

9. The method of claim 1 wherein the column liquid bottom product stream is cooled.

10. The method of claim 9 wherein at least a portion of the bottoms product cooling duty is used to provide heat input to the distillative column.

11. The method of claim 1 wherein the side recovery product is combined with a net production of C4+ bottoms product.

12. The method of claim 1 wherein the side recovery product comprises a hydrogen sulfide-enriched hydrocarbon recovery stream deficient in carbon dioxide.

13. The method of claim 1 wherein the side recovery product comprises a C3+ stream having from about 50 ppm to about 2 molar percent of carbon dioxide or hydrogen sulfide.

14. The method of claim 13 wherein the C4+ product stream comprises from about 1 to 12 molar percent of C4.

15. The method of claim 1 which includes admixing the side recovery stream and a portion of the C4+ alkane stream and withdrawing a C3/C4+ product stream.

16. The method of claim 1 which includes recycling a portion of the condensed product stream into the upper 20% of the distillative column.

17. The method of claim 1 wherein the column bottom product recycle stream contains less than about one molar percent of $C_3$.

* * * * *